United States Patent [19]

Chen

[11] Patent Number: 5,334,215
[45] Date of Patent: Aug. 2, 1994

[54] PINCERS HAVING DISPOSABLE END MEMBERS

[76] Inventor: Shih-Chieh Chen, No. 3, Lane 68, Liou Yang East Street, Taichung, Taiwan

[21] Appl. No.: 119,544

[22] Filed: Sep. 13, 1993

[51] Int. Cl.⁵ .............................................. A61B 17/30
[52] U.S. Cl. ................................... 606/210; 294/99.2
[58] Field of Search ................................ 606/205–211, 606/51, 52; 294/99.2

[56] References Cited

U.S. PATENT DOCUMENTS 4,452,106 6/1984 Tartaglia ............................ 606/210

FOREIGN PATENT DOCUMENTS 2491325 4/1982 France ............................... 606/210

*Primary Examiner*—Stephen C. Pellegrino
*Assistant Examiner*—William Lewis
*Attorney, Agent, or Firm*—Morton J. Rosenberg; David I. Klein

[57] ABSTRACT

A pair of pincers include two legs having one end resiliently secured together to allow the legs to move away and toward each other. Each of the legs has a free end to which are secured a pair of end members. The end members can be disengaged from the free ends of the legs, such that the end members are disposable after use.

2 Claims, 1 Drawing Sheet

PINCERS HAVING DISPOSABLE END MEMBERS

BACKGROUND OF THE INVENTION

1. Field of the Invention

The present invention relates to a pair of pincers, and more particularly to a pair of pincers having disposable end members.

2. Description of the Prior Art

Typical pairs of pincers for medical use comprise a pair of resilient legs movable away and toward each other so as to form the pincers, the end portions of the legs should be carefully cleaned after each medical operation, the end portions are formed integral with the legs and can not be disengaged from the legs.

The present invention has arisen to mitigate and/or obviate the afore-described disadvantages of the conventional pincers.

SUMMARY OF THE INVENTION

The primary objective of the present invention is to provide a pair of pincers which includes a pair of legs each having an end portion that can be disengaged from the respective leg after medical operation.

In accordance with one aspect of the invention, there is provided a pair of pincers comprising two legs having one end resilient secured together to allow the legs to move away and toward each other, each of the legs including a free end, a pair of end members, and a pair of securing means for securing the end members to the free ends of the legs respectively and for allowing the end members to be disengaged from the legs after usage.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
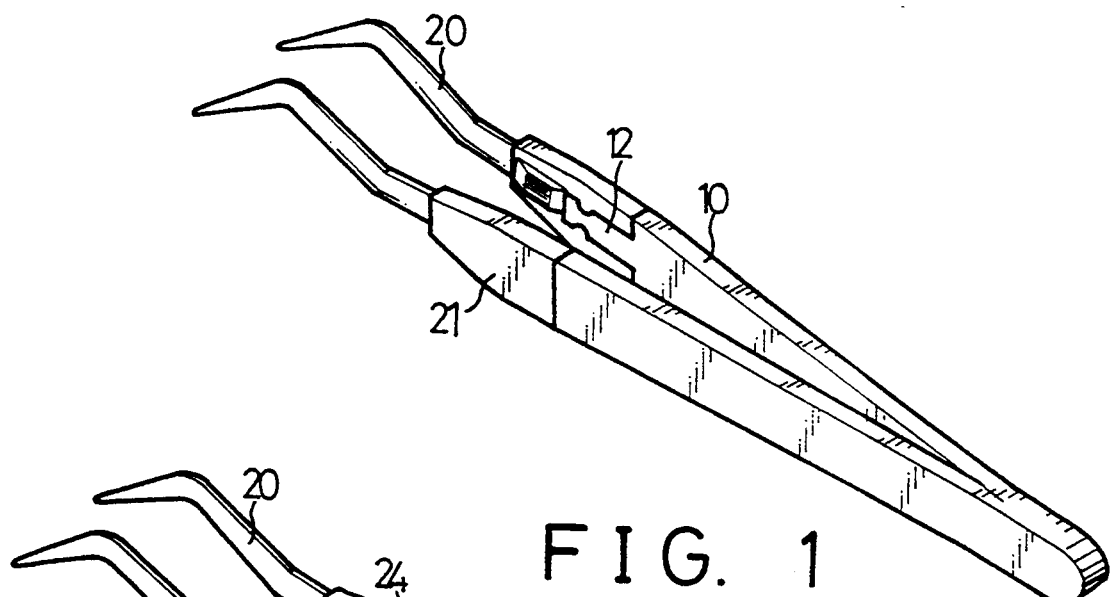
FIG. 1 is a perspective view of a pair of pincers in accordance with the present invention.
Figure 2:
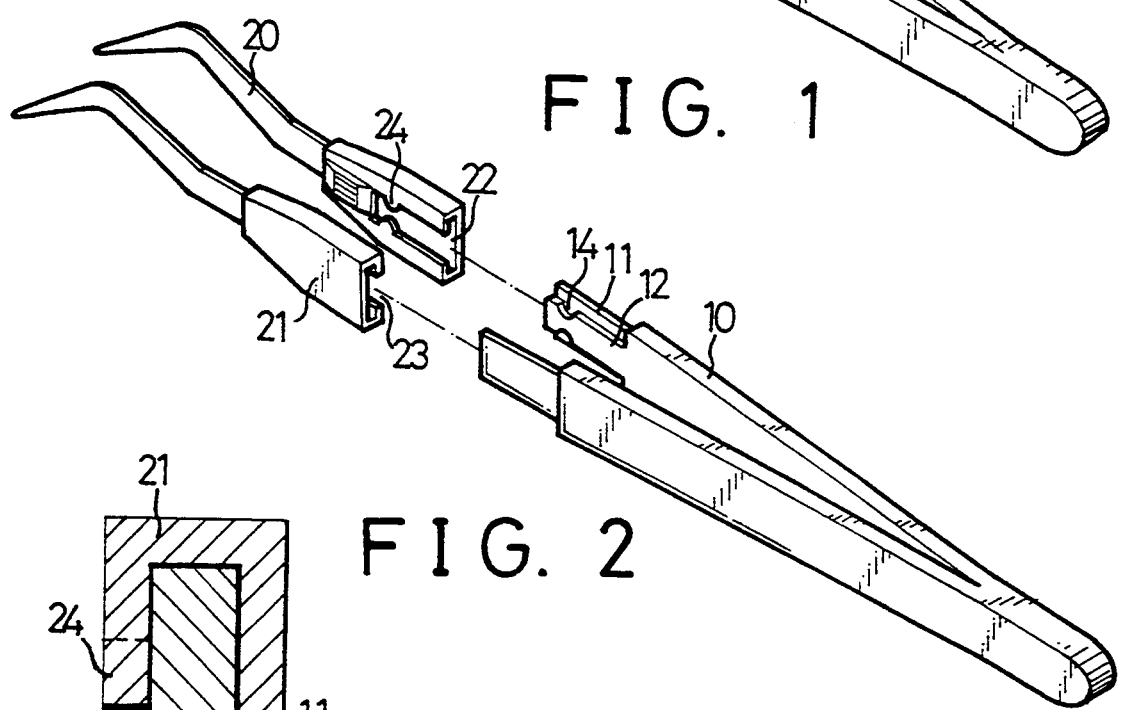
FIG. 2 is an exploded view of the pincers.
Figure 3:
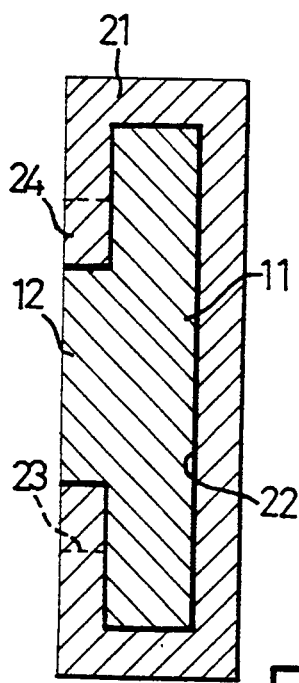
FIG. 3 is a cross sectional view taken along lines 3—3 of FIG. 1.

Referring to FIGS. 1 to 3, a pair of pincers in accordance with the present invention comprises a pair of legs 10 including a first end resiliently secured together and movable away and toward each other in a conventional way, and including a second end which is a free end. An extension 11 extending from each of the respective second ends of legs 10, and a rib 12 formed on each of the extensions 11 are provided. Each rib 12 is formed with two depressions 14 formed on opposing sides thereof. A pair of end members 20, each including a coupler 21, are secured to respective extensions 11. The couplers 21 are preferably made of plastic materials and are secured integrally with the end members 20. For example, the end members 20 are solidly secured in the couplers 21 when the couplers 21 are formed in a molding or mold injection process. Each of the couplers 21 include a channel 22 formed therein for engagement with a respective extension 11 of one of legs 10. A groove 23 is formed in each of the couplers 21, each groove 23 being in open communication with the channel 22 for engagement with a respective ribs 12. Each of the couplers 21 having a pair of projections 24 formed on opposing sides of the groove 23 for respective engagement with the depressions 14 of a respective ribs 12, such that the end members 20 can be easily coupled to the legs 10 of the pincers and can be easily disengaged from the legs after usage.

Accordingly, the pincers in accordance with the present invention includes a pair of disposable end members 20 which can be easily disengaged from the legs after usage.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A pair of pincers comprising:

two legs, each of said legs having one end resiliently secured together to allow opposing free ends of said legs to move toward and away from each other;

a pair of end members releasably coupled to said free ends of said legs; and, means for releasably securing each of said pair of end members to a respective one of said fee ends of said legs, said releasable securing means including (1) an extension extending from each of said free ends of said legs, (2) a rib formed on each of said extensions, and (3) a coupler secured to each of said pair of end members, each of said couplers including (1) a channel for engagement with a respective extension of said legs, and (2) a groove for engagement with a respective rib, whereby, each of said end members are secured to a respective one of said legs.

2. A pair of pincers according to claim 1, wherein each of said ribs includes at least one depression formed therein, and each of said couplers includes at least one projection formed therein for engagement with said depression of said rib so as to secure said end members to said legs.

* * * * *